(12) United States Patent
Lee et al.

(10) Patent No.: US 10,626,472 B2
(45) Date of Patent: Apr. 21, 2020

(54) FREEZE-DRIED COMPOSITION

(71) Applicant: FLUOROGENICS LTD., Salisbury, Wiltshire (GB)

(72) Inventors: Martin Lee, Salisbury (GB); Diane Lee, Salisbury (GB); Mark Laverick, Salisbury (GB)

(73) Assignee: Fluorogenics Ltd, Wiltshire (GB)

( * ) Notice: Subject to any disclaimer, the term of this patent is extended or adjusted under 35 U.S.C. 154(b) by 70 days.

(21) Appl. No.: 14/763,244

(22) PCT Filed: Jan. 28, 2014

(86) PCT No.: PCT/GB2014/050208
§ 371 (c)(1),
(2) Date: Jul. 24, 2015

(87) PCT Pub. No.: WO2014/114956
PCT Pub. Date: Jul. 31, 2014

(65) Prior Publication Data
US 2015/0361511 A1 Dec. 17, 2015

Related U.S. Application Data

(60) Provisional application No. 61/757,300, filed on Jan. 28, 2013.

(30) Foreign Application Priority Data

Jan. 28, 2013 (GB) .................................. 1301457.6

(51) Int. Cl.
| C12Q 1/70 | (2006.01) |
| A61K 9/19 | (2006.01) |
| C12N 9/12 | (2006.01) |
| A61K 47/26 | (2006.01) |
| C12Q 1/6876 | (2018.01) |

(52) U.S. Cl.
CPC .............. *C12Q 1/701* (2013.01); *A61K 9/19* (2013.01); *A61K 47/26* (2013.01); *C12N 9/1252* (2013.01); *C12Q 1/6876* (2013.01); *C12Q 2600/158* (2013.01)

(58) Field of Classification Search
None
See application file for complete search history.

(56) References Cited

U.S. PATENT DOCUMENTS

| 5,338,671 A | 8/1994 | Scalice et al. |
| 5,586,287 A | 12/1996 | Okumura et al. |
| 5,677,152 A | 10/1997 | Birch et al. |
| 7,919,294 B2 * | 4/2011 | Franco De Sarabia Rosado ........ C12N 9/96 435/183 |
| 2002/0173016 A1 | 11/2002 | Wurst et al. |
| 2011/0159497 A1 * | 6/2011 | Lee ...................... C12Q 1/6806 435/6.12 |
| 2012/0142070 A1 * | 6/2012 | Battrell ................ C12N 9/1252 435/188 |

FOREIGN PATENT DOCUMENTS

| WO | 91/18091 A1 | 11/1991 |
| WO | 98/00530 A1 | 1/1998 |
| WO | 02/088387 A2 | 11/2002 |
| WO | 2006/003439 A2 | 1/2006 |
| WO | 2008/036544 A1 | 3/2008 |
| WO | 2008/155524 A1 | 12/2008 |
| WO | 2010/001162 A1 | 1/2010 |
| WO | 2010/061193 A2 | 6/2010 |
| WO | 2010/144682 A1 | 12/2010 |
| WO | 2014/114956 A1 | 7/2014 |

OTHER PUBLICATIONS

GB Patent Application No. 1208808.4, titled "Novel Consumable", filed May 18, 2012; 19 pgs.
GB Search Report from related Application No. GB1301457.6, dated Jul. 25, 2013; 5 pgs.
International Search Report and Written Opinion from related International Application No. PCT/GB2014/050208, dated Jun. 10, 2014; 17 pgs.
Prestrelski et al., "Optimization of Lyophilization Conditions for Recombinant Human Interleukin-2 by Dried-State Conformational Analysis Using Fourier-Transform Infrared Spectroscopy", Pharmaceutical Research, 1995, pp. 1250-1259, vol. 12, No. 9.
Yoshioka et al., "Significance of Local Mobility in Aggregation of β-Galactosidase Lyophilized with Trehalose, Sucrose or Stachyose", Pharmaceutical Research, 2007, pp. 1660-1667, vol. 24, No. 9.
Higashiyama, "Novel functions and applications of trehalose", Pure Appl. Chem., 2002, pp. 1263-1269, vol. 74, No. 7.
Definition of "Stachyose", Chemical Book, Stachyose CAS#:470-55-3, retrieved Jan. 10, 2019; www.chemicalbook.com/ProductChemicalPropertiesCB8412812_EN.htm; 2 pgs.

* cited by examiner

*Primary Examiner* — Iqbal H Chowdhury

(57) ABSTRACT

The invention relates to the use of a polysaccharide having at least four saccharide units, such as stachyose, as a glass-forming agent for the freeze-drying of a reaction mixture comprising an enzyme. In particular, the enzyme is a polymerase useful in a nucleic acid amplification reaction such as a Polymerase Chain Reaction. Compositions comprising such polysaccharides as well as methods for preparing them, kits containing them and methods for using them form further aspects of the invention.

16 Claims, 5 Drawing Sheets

Time = 0 Minutes

Time = 16 Minutes

Time = 32 Minutes

Time = 48 Minutes

Time = 64 Minutes

Time = 80 Minutes

FREEZE-DRIED COMPOSITION

The present invention relates to freeze-dried compositions, in particular those used to carry out chemical or biochemical reactions and containing a polymerase, as well as methods for preparing these and their use.

Lyophilization or freeze-drying is a well-known technique for preserving a wide range of moieties including chemicals, biochemicals and biological samples. It is well known that these moieties need to be mixed with reagents such as stabilisers. A variety of stabilisers are known and these are required to ensure that during the freeze drying process, the moieties retain their structure and function.

In a particular instance, some or all of the reagents necessary for carrying out specific chemical or biochemical reactions are combined and the mixture frozen or freeze-dried. The resulting material can then be stored or transported to the laboratory or environment in which the reaction is later carried out, for example by addition of a sample which may for instance, be a clinical, environmental or other biological sample that requires testing. Freeze-dried material provides a more convenient form for storage and transportation as there is no requirement for refrigeration.

A particular reaction in which this procedure has been used is nucleic acid amplification methods such as the Polymerase Chain Reaction (PCR). In this reaction, specific nucleic acid sequences are multiplied or amplified by subjecting a sample containing that nucleic acid to a series of iterative steps. Primers that are specifically designed to hybridise to the target nucleic acid sequence are included in the reaction and are extended by polymerase enzymes and in particular thermally stable polymerases present in the reaction mixture to produce copies of the target in an exponential manner. The progress of the reaction may be monitored in real time, using labelled probes or other fluorescent moieties that are arranged to produce a variety of labelling systems.

The target nucleic acid sequences amplified may be DNA or RNA. Where the target nucleic acid is DNA, the polymerase used will be a DNA dependent DNA polymerase. In the case of RNA being the target, the amplification product is either the complementary cDNA or RNA and it is produced in a particular variant of PCR known as reverse-transcriptase PCR or RT-PCR. This reaction uses either an RNA dependant DNA polymerase or an RNA/DNA dependant DNA polymerase as a reverse-transcriptase enzyme to produce the cDNA (covert RNA to RNA). As used herein, references to the polymerase chain reaction or PCR include RT-PCR as well as conventional PCR and the term 'polymerase' includes both DNA polymerase and reverse-transcriptase.

Whilst the primers and probes will be specific to particular reactions, there are other reagents, in particular polymerase enzymes, nucleotides, buffers and salts such as magnesium salts that are common to all such reactions. These form elements of so-call 'core master-mixes' and these are available ready mixed from commercial sources. These may be frozen or freeze-dried as discussed above, and so called 'PCR-ready beads' are available. Where specific PCRs are conducted on a regular basis, for instance, for a particular diagnostic purpose, the primers and probes or other label reagents required may be incorporated into the freeze-dried reagent mixture so that they are ready for use directly on addition of a suitable sample.

Freeze-drying of such complex mixtures requires a careful consideration of the stabilising reagents that may be included. These are required to protect the reagents and in particular the biologically active reagents such as the enzymes during the freeze-drying process, but they must not then inhibit or affect the subsequent reaction that is carried out using the freeze-dried mixture.

Various stabilising agents have been suggested for use in this case. For instance US Patent No. 2002/0173016 suggests that a combination of a low molecular weight sugar (which may itself be a combination of di- and trisaccharides) and a starch provides a suitable stabilizing composition for lyophilisation of polymerase containing reaction mixtures. WO2010/001162 teaches that the trisaccharide raffinose and in particular raffinose pentahydrate is a suitable glass-forming agent for use in such reaction mixtures in particular where fluorescent reagents are also present.

Although higher molecular weight sugars such as stachyose have been used previously as a stabiliser in freeze-drying of some pharmaceutical proteins (Prestrelski et al, Pharmaceutical Research, (1995) 12, 9 p 1250-1259), these are generally thought to be less effective than lower molecular weight sugars in relation to the freeze-drying of the enzyme β-galactosidase (Yoshioka et al. Pharmaceutical Research (2007) 24, 9, 1660-1667).

The applicants have found that higher molecular weight saccharides are particularly beneficial glass-forming agents for use in freeze-drying, in particular of chemical and biochemical reaction mixtures comprising a range of enzymes, in particular those that are useful in the manipulation of nucleic acids such as polymerases.

According to the present invention there is provided the use of a polysaccharide having at least four saccharide units as a glass-forming agent for the freeze-drying of a reaction mixture comprising an enzyme other than β-galactosidase.

In particular, the enzyme is not an enzyme that breaks down sugars.

In a particular embodiment, the enzyme may be an enzyme that has an effect on nucleic acid, protein or pyrophosphate. Such enzymes may be selected from the group consisting of polymerase, DNAse, RNAse exonucleases, nuclease inhibitors, restriction enzymes, uracil DNA glycosylase, protease or pyrophosphatase.

In a particular embodiment, the enzyme is a polymerase.

The polysaccharide suitably comprises from 4 to 8 and preferably from 4 to 6 saccharide units. In particular, the saccharide is selected from stachyose, verbascose and lycopose. A particularly preferred saccharide is stachyose.

Whilst pure saccharide may be used, a good source of saccharide material are natural product extracts that may contain a variety of saccharides including some which have less than 4 saccharide units. However, provided a substantial portion of the saccharides present, in particular at least 50%, such as at least 60%, 70%, 80%, 90% or 95% have at least 4 saccharide units, a beneficial effect can be found.

In particular, by using the higher molecular weight sugars such as stachyose as the major stabilizing element of the mixture, the applicants have found that freeze-dried compositions obtained have improved resistance to hydration on exposure to moisture in for example the air. It would appear that the sugar is acting as a more effective dessicant, and this increases the longevity of the composition.

However, in addition, compositions containing these sugars can be designed to have better dissolution properties than formulations containing lower molecular weight sugars, as the amount of other high molecular weight excipients that tend to reduce solubility, can be reduced. In addition, the sugars solutions have a longer shelf life than similar solutions of lower molecular weight sugars making them easier to handle and store during the manufacturing process. Furthermore, sugars such as stachyose gets into solution better than raffinose, which requires gentle warming to get it into solution. Furthermore, raffinose has a tendency to precipitate out when stored in solution at low temperatures as are found in a refrigerator, whereas stachyose and some other high molecular weight sugars do not. This means that solutions derived from compositions containing stachyose may be easily stored in a fridge and show reduced spoilage as a result of bacterial contamination.

In particular, according to a further aspect of the present invention there is provided a composition comprising:
(i) an enzyme other than β-galactosidase;
(ii) a polysaccharide comprising at least 4 saccharide units.

The composition is suitably in a freeze-dried form. Alternatively, it is in the form of a solution ready for freeze-drying or as a solution reconstituted from said freeze-dried form.

The enzyme may be any of the enzymes listed above, but is suitably an enzyme that impacts on nucleic acid such as a polymerase. A variety of polymerases are known and these selected depending upon their intended purpose in a reaction. For instance, there are a range of isothermal amplification reactions such as the transcription mediated amplification, nucleic acid sequence-based amplification, signal mediated amplification of RNA technology, strand displacement amplification, rolling circle amplification, loop-mediated isothermal amplification of DNA (LAMP), isothermal multiple displacement amplification, helicase-dependent amplification, single primer isothermal amplification, and circular helicase-dependent amplification as well as whole genome amplification, where the polymerase used need only be active at the temperature at which the reaction is carried out.

In a particular embodiment, the polymerase is a thermostable polymerase such a Taq polymerase or Pfu or a reverse-transcriptase enzyme such as MMuLV, AMV or Tth that is used in reactions such as the polymerase chain reaction which involve thermal cycling, including stages carried out at high temperatures. The polymerases may be recombinant to form enhanced thermostability or processivity, or other property, for example they may include fusion proteins combining DNA binding domains with a polymerase. The thermostable polymerase maybe chemically modified or otherwise blocked so that it is inactivated until subject to an initial heat activation step, as used in a conventional 'HotStart' PCR. Such enzymes are available from a variety of commercial sources and are described for example in U.S. Pat. No. 5,677,152. The polymerase may also form an antigen to antibody conjugate (Taq and anti-Taq antibody) as to facilitate a hot start as described for example in U.S. Pat. No. 5,338,671 or U.S. Pat. No. 5,586,287). Other modifications or co-reactant species used to facilitate a hotstart such as aptamers, peptides or other species.

The polymerase enzyme is suitably present at a concentration that will allow it to carry out a reaction such as a PCR when the composition of the invention in freeze-dried form is reconstituted. This will depend upon factors such as the volume of the freeze-dried composition used and the volume of the reconstituted reaction mixture. However, in general polymerase is present in a reaction such as a PCR in concentrations of from 0.01 units/uL (10000 UNITS/L) to 0.2 units/uL (200000 UNITS/L) and this may typically be achieved by ensuring that the freeze-dried composition contains from 10000-200000 units/L in particular from 40000 units/L where a 'unit' is defined as the amount of enzyme that will incorporate 15 nmol of dNTP into acid-insoluble material in 30 minutes at 75° C.

As set out above, the saccharide suitably has from 4 to 8 and preferably from 4 to 6 saccharide units. In particular, the saccharide is selected from stachyose, verbascose and lycopose. A particularly preferred saccharide is stachyose. The polysaccharide may comprise a mixture of saccharides such as found in an extract from a natural product. There is no need however for the addition of starch or other components.

The polysaccharide must be present in a glass-forming amount in the composition. This will vary depending upon the other components present in the mixture. Where the salt content of a reaction mixture is high, the levels of polysaccharide may need to be increased to achieve the desired protective effect. However, the polysaccharide should not be present in such a significant amount that upon reconstitution of the composition by addition of water to produce a "final composition" for use in a chemical or biochemical reaction, it is present in such an amount that it inhibits or otherwise restricts the reaction. The amount in a final composition is typically no more that 10% m/v for example from 0.5 to 10% m/v and suitably from 1-20% m/V for the solution used to form the lyophilised glass substrate. The relative volume of the composition before and after freeze-drying will vary depending upon the amount of water required to solubilise the components to form the admixed composition. In general however, the volume of the composition pre-lyophilisation will be from 0.1 to 0.5 times the volume of the composition after lyophilisation and dissolution/reconstitution, and suitably about half the volume. This means that typically, the amount of sugar present in the freeze-dried composition or 'cake' is from 0.5 to 5% m/v for instance about 2.5% m/v.

The composition may further comprise additional components required in order to carry out a chemical or biochemical reaction such as the polymerase chain reaction. In particular, the reaction mixtures may further comprise a buffer used in the PCR reaction, in particular a buffer having a pH of from 7-9 for instance from 8 to 9. Suitable buffers include Tris or Trizma buffers as well as HEPES, tricine and bicine buffers in some cases. Where the buffer is not included in the composition, it would be necessary to ensure that a suitable rehydration buffer is used to reconstitute the dried composition ready for use. The amount of buffer present in the composition will be such as to ensure that when the freeze-dried composition is reconstituted, it will produce a concentration of buffer in the final reaction mixture in accordance with that which is conventional in the art, depending upon the particular buffer employed. For instance, Tris buffer concentrations in the range of from 1-50 mMol/l may be used, such as from 5-35 mMol/L and in particular from 10-20 mMol/L are generally required in final amplification reaction mixtures and so appropriate concentrations will be added to the composition before lyophilisation.

Similarly the composition may further comprise salts required for use in the reaction. In the case of PCR, such salts will be for example magnesium, sodium, lithium, potassium, ammonium or manganese salts, such as halide salts for example chlorides or sulphates. A particular salt that is used in this way is magnesium chloride ($MgCl_2$). Salts will be present in an amount that is necessary for carrying out the reaction. Thus in the case of polymerase chain reaction, salts and in particular magnesium salts may be present in the freeze-dried composition in an amount of from 1-10 mM and suitably from 1.5-6 mM such as from 3-6 mM to produce suitable salt concentrations on reconstitution. However, it has been reported that the presence of salts can lead to instability in the composition and so again the necessary salts may be omitted from the composition and added subsequently with the rehydration buffer if required. In this embodiment, the salts may be included in a kit comprising the composition and the necessary salt supplements.

Alternatively, the salts such as magnesium may be present but in concentrations which are lower than are required for use in the reaction, for example at concentrations of less than 500 µM. As described in WO2006/003439, it has been found that such small amounts of magnesium salts may in fact be beneficial to the stability of the composition. In this case, supplementary salts will be included in the rehydration buffer.

Generally, compositions used for reactions such as the polymerase chain reaction will include the nucleotides that form the building blocks of the amplification product. These may include deoxy or deaza nucleotides containing GATC or U nucleosides or their derivatives. In some cases, the nucleotides themselves will be fluorescently labelled. These are available from a variety of commercial sources. They will be present in the freeze-dried composition in a concentration that will provide a suitable concentration of nucleotides in the reaction mixture reconstituted from it. This will depend upon the volume of the freeze-dried composition and the final volume of the reaction mixture reconstituted from it. Typically, a PCR requires a concentration of each nucleotide of from 50 µM to 8000 µM and this may generally be achieved by including nucleotides in the composition of the invention in freeze-dried form of from 0.1 to 1 mM, for example from 0.2 to 0.4 mM.

In a particular embodiment, a blocking compound, as is conventional in PCR reaction mixtures, may be included in the composition. The blocking compound is believed to function by preventing inhibition of the PCR by interaction with the vessel walls, for example by preventing leaching of metals or sequestering any metals which may leach from the walls in the course of the reaction. It may also reduce abstraction of enzyme and nucleotides to the reaction vessel wall. The nature of the blocking compound will depend upon the nature of the vessel into which it is intended that the reaction should be conducted.

Particular examples of blocking compounds are glass coating or glass blocking compounds such as bovine serum albumin (BSA) either alone or in combination with other blocking materials such as gelatine. Gelatine may be obtained from a variety of sources including bovine, pig, seaweed (carrageenan) or fish gelatine as described in WO2008155524.

Blocking agents are suitably included in effective amounts which will depend upon the particular compound selected. However, for BSA for instance, the amount is suitably sufficient to provide from 0.1 to 1 mg/ml and preferably about 0.25 mg/ml in the final reaction composition (i.e. the composition made up for carrying out the chemical or biochemical reaction). Gelatines will suitably be present in an amount in the range of from about 0.0025%-0.01% m/v or about 0.0025%-0.01% w/w. Care should be taken that the amount of blocking agent is not sufficiently high so as to significantly inhibit the final reaction.

The compositions suitably further comprise an anti-oxidant and/or anti-maillard reagent. The applicants have found that threonine works as a particularly effective anti-oxidant and/or anti-maillard agent, and enhances the stability of the freeze-dried composition. Either L- or D-threonine is used. The threonine appears to react with any oxygen produced, or as a result of ingress into the resulting product and therefore assists in the stabilisation of the mixture.

Furthermore, it has been found that the presence of threonine may stabilise the signalling achievable from fluorescent labels included in the composition, in particular when stored at elevated temperatures.

The amount of threonine in the composition will vary depending upon the precise nature of the composition. It is suitably selected so that it does not affect the pH of the composition, which may be important in some chemical or biochemical reactions. Typically however, it may be present in the final reaction composition in an amount of from 1-20 mM/L, for example at about 5 mM/L. As discussed above, this means that the threonine will be present at a higher concentration, for example, at approximately twice these concentrations in the freeze-dried compositions.

When a composition is freeze dried in the presence of a glass-forming reagent, it generally forms a "cake" type 3-dimensional structure. This structure is optionally supported by the inclusion of a suitable stabiliser for the cake structure, and so this is a further component of the mixture.

Examples of suitable stabilisers that may be included in the composition include polymeric compounds such as polyethylene glycol (PEG), polyvinylpyrrolidine (PVP) and or polysaccharides such as Ficoll or Dextran. In a particular embodiment, however, the stabiliser is omitted or used at reduced concentrations within the composition as it has been found that compounds such as PEG may contribute to the inhibition of fluorescent signals. It may also reduce solubility of the overall compositions described above. In the context of the compositions of the present invention, the use of high molecular weight sugars as the glass-forming agent means that the amount of stabiliser used in the final composition may be less than 4% M/v, for instance less than 1% M/v for example less than 0.8% for 0.1-0.5% M/v such as about 0.25 M/v %. In the freeze dried compositions and cake therefore, there will typically be less than 2% M/v, for example from 0.2 M/v to 1% M/v for instance only about 0.5% M/v stabliser present.

As mentioned above, the precise enzymes and other reagents present will be selected depending upon the particular nature of the chemical or biochemical reaction being effected. They may include reactions carried out on multiple or repeated occasions such as diagnostic tests, screening tests, nucleic acid amplification reactions, nucleic acid sequencing reactions etc.

In addition, where the polymerase enzyme is not chemically or otherwise 'blocked' as discussed above, alternative 'Hot Start' technologies may be incorporated into the composition by inclusion of suitable addition components. For instance, it is possible to add an anti-Taq DNA polymerase antibody such as those available from Clontech, Sigma or Invitrogen, as a further component of the composition. Such antibodies bind to the active site of the polymerase and inactivate it at ambient temperature to form an antigen to antibody conjugate of the type discussed above. However, the antibody denatures and dissociates from the enzyme at elevated temperatures used during the amplification cycles and so the enzyme becomes active. The relative amount of any anti-Taq antibody included in the composition is suitably sufficient to ensure that it is able to fulfill the function of inhibiting the Taq enzyme until it is required. Generally therefore an excess of anti-Taq antibody as compared to Taq enzyme will be used. Thus for example for every unit of Taq enzyme in the composition, at least 1.5 and preferably at least 2 units of anti-Taq antibody will be included. Taq antibody is usually sold by the µg and the concentration is very dependent upon the source and quality of the antibody as well as the nature of the assay. Too much antibody may be detrimental and can actually cause more primer dimer in some assays. However, the precise amount of Taq antibody will be determined in accordance with usual practice and will typically be in the range of 0.001 to 0.004 µg/l final reaction mixture.

Yet another Hot-Start methodology involving the use of a combination of an inhibitory amount of a pyrophosphate salt to prevent primer extension taking place, and a pyrophosphatase enzyme which digests this pyrophosphate at elevated temperatures, to allow the PCR to progress is described in WO 02/088387.

In this case, the pyrophosphate salt and the pyrophosphatase enzyme may be included as further components of the composition of the invention.

If required, the composition may comprise further elements that may be useful in the reaction, such as the PCR. A particular example of such an element may comprise a nucleic acid that is able to act as an internal control for the amplification reaction. This nucleic acid may be a 'homologous' nucleic acid which is recognized by the same primers as the target nucleic acid in the sample, but which produces different and distinguishable product, for example of a different size. Alternatively, it may be heterologous nucleic acid which is amplified by a different set of primers, which are, in that case also included in the composition, so as to yield a different product which is clearly distinguishable from the amplification target. In either case, the presence of the product of amplification of the nucleic acid acting as internal control will provide confirmation that the amplification conditions have been effective and that therefore amplification of target, if present, would be expected.

The enzyme such as the polymerase used in the composition is, as discussed above, obtainable from a variety of sources. Generally however, as supplied, the enzyme is in the form of a wet reagent which includes a range of excipients including detergents, anti-oxidants, anti-reducing agents and significant quantities of solvent which is generally glycerol but in some cases, oligosaccharide solutions are used. For example, some polymerase enzymes are supplied as a 50% glycerol solution, the latter being present to assist with freeze-thawing carried out during the enzyme production and storage process. Removal of the glycerol is necessary to effect an efficient freeze-drying process however. The applicants have found that substantially complete removal of glycerol is beneficial to the freeze-drying process so that the composition is substantially free of glycerol. In particular the composition should contain less than 1% v/v glycerol, for example less than 0.5%, 0.22%, 0.11% or 0.01% vv glycerol. Suitably, the composition is free of glycerol.

Removal of glycerol from commercial polymerase preparations can be effected using a variety of conventional techniques including for instance separation based upon molecular weight, such as dialysis, microfiltration using a membrane or exclusion chromatography for instance on a Sepharose™ column, or separation based upon affinity techniques such as ligand binding, histadine tagging, or by using specific binding partners such as antibodies or aptamers.

In a particular embodiment, one or more washing steps using a buffer such as a Tris buffer are carried out during or subsequent to the removal procedure to ensure substantially complete removal of glycerol.

At this stage, it may be necessary to re-introduce the other agents such as detergent, anti-oxidant and anti-reducing agent that facilitate the activity of the enzyme during the reaction since these components may be lost during such a thorough removal procedure. Generally, the specific reagents which tailor a PCR to the particular target, such as the primers and any probes required for example for use in connection with a real-time PCR, are specific to a particular area of application such as research and so added when the freeze-dried composition is reconstituted into a reaction mixture for use. However, in many cases, in particular in the diagnostics field, the targets are the same in many cases, and therefore the inclusion of oligonucleotides that act as probes and primers into the freeze-dried composition is convenient, so that the composition becomes assay specific is desirable for ease of use.

Alternatively, one or more separate compositions comprising oligonucleotides that act as probes and/or primers as well as salts or buffer compositions required to carry out the reaction, may be prepared separately and conveniently these may also be dried. They may be freeze-dried but in some cases, they may be dried using other methods such as air drying, or dried by direct application of heat to cause evaporation of the solvent (e.g. water, ethanol), rather than sublimation as occurs in freeze drying.

For example, using this approach, buffers or salts including potential enzyme cofactors, that may be required for the final reaction, but which could be inhibitory, for example, to the stability of the polymerases during and post drying to be stored separately from the enzymes before use. Examples of such buffers or salts may include ammonium sulphate but there are others as would be appreciated by the skilled person. An example of an enzyme cofactor which may be dried and stored separately is magnesium or manganese ions in the form of salts such as magnesium chloride. Such enzyme co-factors could be dried separately to form an additional or alternative separate compositions, or conveniently, these may be included in the dried buffer composition as a single second composition. Keeping the buffer components and/or co-factors separate in this way suppressed the polymerase activity of the enzyme until it is re-suspended using the reconstitution buffer, thus further improving the stability of the composition.

Such additional compositions may be re-hydrated by the end-user before use. Depending upon the content of the second composition, they may be reconstituted using a solution of any residual components required in the reaction, for example using a cocktail of primers and probes in solution that are required to complete their specific amplification reaction, or a reconstitution buffer solution if the buffer components are not already included in the composition.

However, in a particular embodiment, it may be convenient to provide probe and/or primer compositions in dried form and separately, in particular in kits where a single mastermix may be required to be used in a variety of different amplification reactions.

In such cases, where the second composition is freeze-dried, it may be convenient, although not essential, to utilise similar glass-forming agents as those described above. The applicants have found that polysaccharides such as stachyose provide effective glass-forming agents for such compositions including oligonucleotide compositions as exemplified below. Thus, in a further aspect the invention provides a kit comprising the composition of the invention and a second composition in dried form, for example in freeze-dried form, said second composition comprising a reagent, such as an oligonucleotide useful as a probe or primer in a nucleic acid amplification reaction and/or buffer reagents such as salts, for use in a reaction with said enzyme. The second composition may further comprise stachyose as described above.

Novel compositions such as dried buffer compositions that may be included in said kits as said second compositions form a further aspect of the invention. Thus, in a further aspect, the invention provides a dried composition comprising one or more of the following:

(i) a salt required to carry out a nucleic acid amplification reaction;

(ii) components of a reconstitution buffer useful in an amplification reaction;

(iii) an oligonucleotide capable of acting as a primer in a nucleic acid amplification reaction: and (iv) an oligonucleotide capable of acting as a probe in a nucleic acid amplification reaction.

Any oligonucleotides used in the compositions or second compositions as described above may be labelled as is well known, using for instance a fluorescent label. The composition may further comprise a labelled oligonucleotide, such as a fluorescently labelled oligonucleotide(s) useful in monitoring the progress of a polymerase chain reaction in real time. Other fluorescent agents useful in detection of reactions such as PCR in 'real-time' such as intercalating fluorescent dyes may also be included in the composition. In other assays such as the Plexor® assay, fluorescent mononucleotides are used in the monitoring process and if the composition is intended for use in such an assay, the labelled nucleotides may be included in the composition of the invention.

The amounts of the various components included in the composition will vary depending upon factors such as the precise nature of the particular component; the nature of the PCR which it is intended should be conducted etc. However, this will be determinable in each case using established protocols and procedures as would be understood in the art.

Compositions of the invention are suitably freeze-dried to form a dried cake that may be distributed in the form of pellets and/or beads. In a particular embodiment, sufficient composition to carry out multiple reactions, for example up to 96 or 48 reactions are freeze-dried to form a single large cake in a container. The container should be of sufficient size to allow sufficient water or solvent to be added to reconstitute sufficient solution to effect multiple reactions. Individual reaction mixture volumes may then be dispensed from the container for example using a pipette, to the reaction vessels in which the reaction is to be carried out. Such reaction vessels may include the wells of microtitre plates.

In a particular embodiment however, the compositions of the invention are formed in solution form by mixing the reagents in water, and then freeze-dried in situ to form a cake structure.

In another embodiment the cake structure may be formed from two or more layers of different reagent formulations. The purpose of this may be to enhance either the resulting cake stability and/or the performance of the final reaction upon dissolution. The active formulation of many reactions may compromise the optimum stability of one or more specific components. One or more of these components may be included in a separate reagent layer.

For example, certain fluorophores have a greater stability at particular pH's. Fluorescein derivatives prefer basic environments, whereas, cyanine derivatives prefer neutral pH's which are not consistent with the final amplification optimum range described above. Therefore standard cakes prepared at pH 8-9 would compromise the stability of cyanine fluorophores.

Likewise, polymerases may be delineated into their own layer such that they are not available to interact with specific reaction components such as primers or probes. This would provide a pseudo 'hotstart' during the lyophilisation process, the resulting reaction only becoming active after dissolution of both layers.

Each layer may contain one or more of the reagents from the final amplification formulation together a glass-forming sugar as described above, and any other excipients such as the stabilizer. The layers are formed by dispensing reagents individually and freezing each one before dispensing the next reagent thereover. The resulting structure of frozen layers can then be freeze dried. The precise formulations of each layer would be formulated as to provide a suitable final composition upon co-dissolution, whilst drying to form a single cake structure.

In summary then, layered compositions of this type may be prepared by a process comprising (i) freezing a solution of a polysaccharide as defined above and either one or more of said further components or said enzyme to form a first frozen layer, (ii) adding a second solution of a polysaccharide as defined in claim 1 and a different one of said further components or said enzyme and freezing the second solution into a distinct layer, (iii) optionally repeating step (ii) until all components of the composition are present in one of the frozen layers, and (v) freeze-drying the resultant structure. The cake obtained in this way will also have a layered structure, allowing components of the mixture which are incompatible in some way to be held separately in the cake so that they do not interact significantly before the cake is dissolved for use.

In a particular embodiment, the compositions of the invention are freeze-dried in a reaction vessel suitable for carrying out the ultimate reaction such as the polymerase chain reaction. This means that the compositions may be reconstituted and reacted in the same vessel, avoiding the need to transfer reagents between vessels and so avoiding some contamination risks.

A particularly suitable vessel for holding compositions as described above is as described in co-pending British Patent Application No. 1208808.4. It comprises thermally conducting plastics that allow rapid transfer of thermal energy from the contents during freeze-drying and also rapid transfer of thermal energy during the heating and cooling cycles required for carrying out a PCR. Such vessels may be in the form of single tubes, or multi-well plates such as microtitre plates that conventionally contain 96 individual wells.

Thus such vessels, preloaded with the compositions of the invention in freeze-dried form can be stored, transported and sold ready for use.

In use, the freeze-dried composition is reconstituted by addition of a sample in liquid form together with any components that are required for the reaction but are not present in the composition as discussed above. The thus formed solution is then subjected to appropriate reaction conditions, which, in the case of PCR, is a thermal cycling procedure.

Methods for preparing the composition of the invention and the use thereof form further aspects of the invention.

Thus, in a further aspect, the invention provides a method for preparing a composition as described above in freeze-dried form, which method comprises combining together a polymerase enzyme, a polysaccharide as defined above and optionally one or more of the further components as described above in solution form, and freeze-drying said mixture. Suitably, in a preliminary step, glycerol is substantially completely removed from the polymerase enzyme used as described above.

In a particular embodiment, the liquid composition is divided amongst multiple reaction vessels, which suitably comprise a thermally conducting plastic as described above, so that each vessel contains sufficient reagents to carry out a single reaction using the polymerase enzyme, and freeze-dried within said vessels.

In a further aspect, the invention provides a method for carrying out a chemical or biochemical reaction using a polymerase enzyme, said method comprising forming a reaction mixture by addition of a liquid and any addition components necessary for carrying out said reaction, to a composition as described above in freeze-dried form, and subjecting the thus formed solution to suitable reaction conditions. In particular, the reaction will be a polymerase chain reaction. The use of the polysaccharide as described above provides for excellent storage, stability and dissolution properties of the freeze-dried composition.

The invention will now be particularly described by way of example with reference to the accompanying drawings, in which.

EXAMPLE 1

Preparation of Compositions of the Invention

Figure 1:
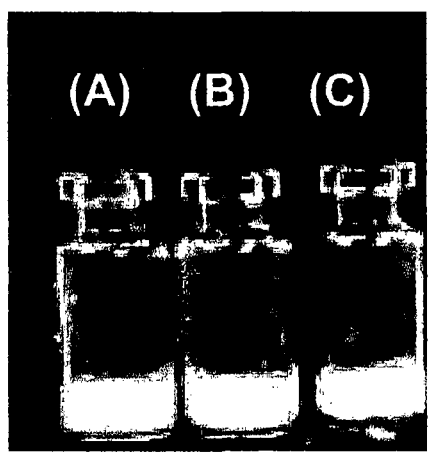
FIG. 1 show the results of a stability trial carried out on a variety of freeze-dried sugar solutions.
Figure 1:
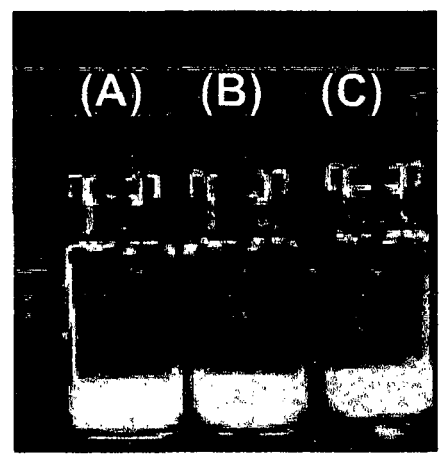
Figure 1:
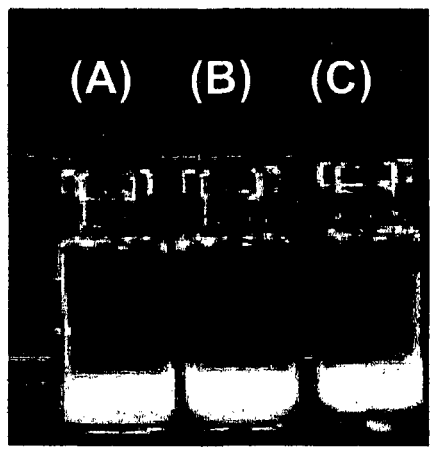
Figure 1:
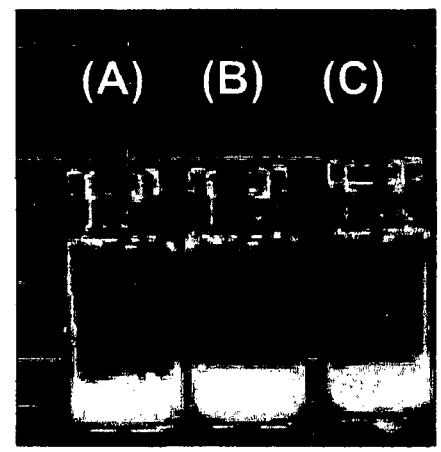
Figure 1:
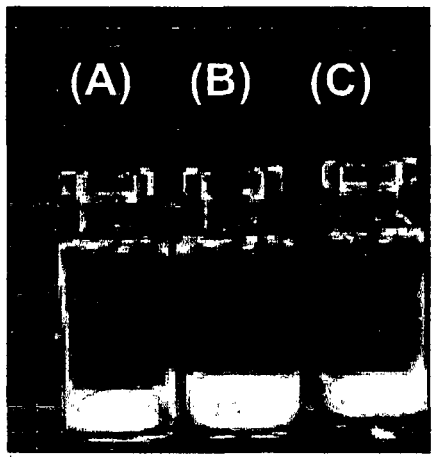
Figure 1:
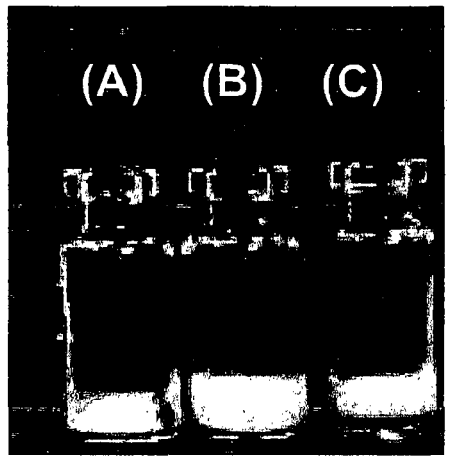

Freeze dried compositions of the invention are prepared by mixing together the components required for the reaction including enzymes and optionally other components discussed above, with a sugar as defined above such as stachyose in a glass-forming amount and a small quantity (less than 1% M/v and preferably less than 0.5% M/v) of a structural stabiliser such as PEG, also as described above. Any enzyme used should be substantially free of glycerol. At this stage, the mixture will contain a solvent and in particular water. The amount of water present is selected to give the desired cake volume after freeze drying. Specifically, during a freeze drying process, the mixture is first frozen, which effectively determines the volume of the cake. During subsequent sublimation of the solvent, the frozen material may undergo some shrinkage, but will generally retain a substantial proportion of the volume of the frozen material. This is useful in that it allows a cake of a suitable volume to be produced. Thus the amount of solvent such as water present in the mixture at this time will vary depending upon factors such as the amount required for dissolution of the components and the desired cake volume. Typically, any solution suitably contains less than 50% water as solvent compared to the final reconstituted reaction composition.

The solution is then freeze-dried to remove substantially all of the water in a freeze dryer used in accordance with the manufacturer's instructions. The freeze-dried composition forms a cohesive and malleable cake.

In particular, the or each container holding the freeze-dried composition is sealed under an inert atmosphere such as a nitrogen atmosphere.

Just prior to use, the freeze-dried compositions are reconstituted by addition of a suitable volume of water which may include a sample under test. The reaction mixture is then processed in the usual way.

It has been found that the freeze-dried compositions of the invention are more stable for prolonged periods, for example in high humidity prior to use, when compared to published methods. They also reconstitute more easily, after exposure to form active reaction mixtures which are extremely reliable in use.

EXAMPLE 2

Comparative Environmental Exposure Properties of Freeze-dried Cakes of Various Sugars The following solutions were prepared:
A) 2.5% (m/v) Raffinose, 0.5% (m/v) PEG, 500 uL cake
B) 2.5% (m/v) Stachyose, 0.5% (m/v) PEG, 500 uL cake
C) 2.5% (m/v) Trehalose, 0.5% (m/v) PEG, 500 uL cake These were each freeze dried to form a similar 500σ cake. The cakes were stored in a desiccator at about 75% humidity in the presence of a saturated solution of sodium chloride at ambient temperature. The stability of the cakes over time was monitored and the results are showed that the stachyose composition (B) retained stability better than both compositions (A) and (C).

The experiment was repeated using slightly larger (525σ) cakes. The materials were placed in glass lyovials, and then dried using a Virtis Advantage+ freeze drier, operating a lyophilisation cycle comprising a thermal treatment step, a primary drying step and a Post hold step as summarised in the following tables:

| Thermal Treatment | | | |
|---|---|---|---|
| Step No | Temp° C. | Time (minutes) | Ramp/Hold |
| 1 | 10 | 15 | Hold |
| 2 | −45 | 110 | Ramp |
| 3 | −45 | 120 | Hold |

| Primary Drying | | | | |
|---|---|---|---|---|
| Step No | Temp° C. | Time (minutes) | Vacuum | Ramp/Hold |
| 1 | −45 | 900 | 100 | Hold |
| 2 | 0 | 120 | 100 | Ramp |
| 3 | 0 | 60 | 100 | Hold |
| 4 | 20 | 50 | 100 | Ramp |
| 5 | 20 | 120 | 100 | Hold |

| Post hold | | |
|---|---|---|
| Temp° C. | Time (minutes) | Vacuum |
| 20 | 1000 | 100 |

Condenser temperature: −55° C.
Secondary Set Point: 45° C.

A bell jar was filled with a saturated sodium chloride solution at ambient temperature to produce an approximate relative humidity environment of ~75%. The caps from the three lyovials were removed immediately before placement within, and closure of, the bell jar. The hydration of the cakes was filmed using time lapse photography.

The results are shown in FIG. 1. These show that the stachyose cake (B) was resistant to collapse showing marginal alteration in cake structure within the period of the experiment (~80 time minutes). The raffinose cake (A)

showed almost complete collapse after ~65 minutes. The trehalose cake (C) showed approximately 50% collapse at the completion point of the experiment (~80 time minutes) minutes.

As a result, stachyose appears to provide a more stable freeze dried composition than either raffinose or trehalose.

EXAMPLE 3

Generation and Testing of a Lyophilised PCR Mastermix

This example illustrates the generation of a lyophilised core master mix preparation according to the invention. This includes the use of a chemically modified hot start polymerase Taq DNA dependent polymerase in a suitable buffer composition dried in a glass lyovial.

Example of freeze dried master mix composition:

| Reagent | Cake Concentration (2x) | Final Concentration (1x) |
|---|---|---|
| Tris | 20 mM | 10 mM |
| MgCl2 | 6 mM | 3 mM |
| BSA | 500 ng/µl | 250 ng/µl |
| dNTPs with dUTPS | 0.4 mM | 0.2 mM |
| Stachyose | 2.5% | 1.25% |
| PEG | 0.5% | 0.25% |
| TAQ polymerase | 0.08 U/µl | 0.04 U/µl |
| TAQ additive* | =0.08 U/µl | =0.04 U/µl |

*TAQ additive is a detergent mix obtainable from Fluorogenics Ltd.

A cake comprising the above components was prepared and was freeze dried in a Virtis Advantage+ freeze drier using the program described in Example 2 to create active lyophilised product having a final concentration as listed above.

The resulting freeze dried mixture was reconstituted by addition of various concentrations of water as detailed below and used to amplify a DNA target (derived from bacteriophage λ) using custom primers in combination with SYBR® Green-1 DNA binding dye to a final concentration of 1:10,000 of reference solution. The mixture was amplified on the Genie thermal cycler using:

PCR Parameters

| | Denature | 95° C. 900 seconds | |
|---|---|---|---|
| | Amplification | 95° C. 20 seconds | |
| | | 55° C. 20 seconds | |
| | | 74° C. 20 seconds | Optical Read X5 |
| 45 Cycles | | | |
| | Melt | 50° C. 20 seconds | |
| | | 95° C. 10 seconds | Continuous read −1 |
| | | | Rate = 0.1° C./second |

Figure 2:
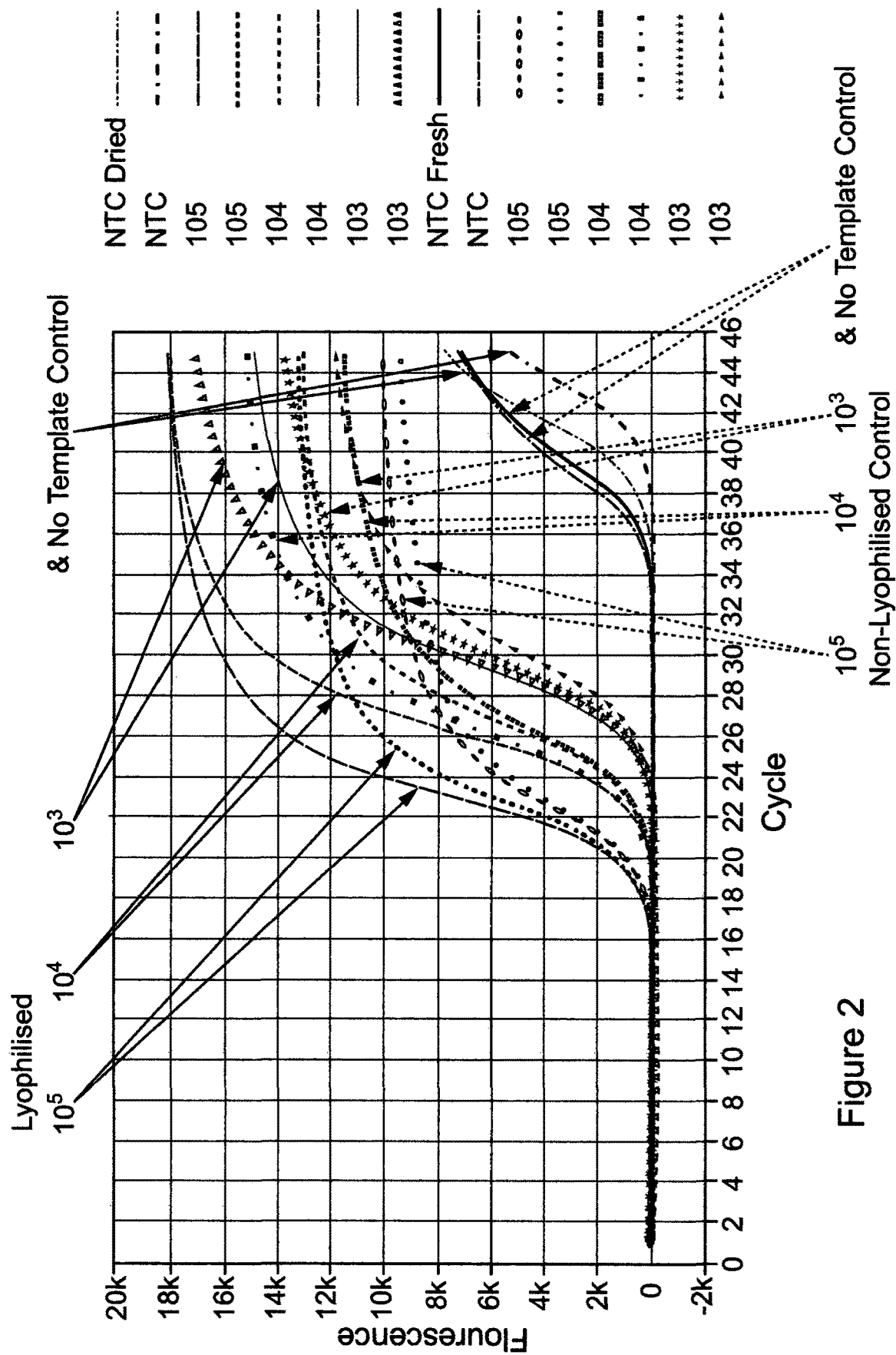
FIG. 2 shows the results of PCR reactions carried out using reaction mixtures in accordance with the invention and fresh undried reaction mixture.

The resulting mixture was used to amplify a DNA target (derived from bacteriophage λ) using custom primers in combination with SYBR® Green-1 DNA binding dye to a final concentration of 1:10,000 of reference solution. The data (FIG. 2) shows three 10-fold dilutions (labelled 10^5, 10^4, & 10^3) of template and a no template control in duplicate amplifications. The solid lines are reactions prepared using lyophilised master mix. The dotted line shows the same formulation prepared as a non-lyophilised control.

The results are substantially equivalent showing that the stachyose has protected the activity of the active components through the freeze-drying process.

EXAMPLE 4

Preparation and Use of a Two-part Composition Kit

A lyophilised core PCR master mix was prepared according to the invention, and a second composition comprising a lyophilised primer and probe mixture was also prepared. The Taq enzyme used in this example was an anti-Taq antibody mediated hot start Taq DNA dependent polymerase in a suitable buffer composition, available from Promega (USA).

Primer Probe Recipe (2× cake formulation), dried to 12.5 µL volume final.

| REAGENT | CAKE CONCENTRATION (2x) | Units |
|---|---|---|
| HSV 1 F | 1 | uM |
| HSV 1 R | 1 | uM |
| HSV 1 P | 0.4 | uM |
| HSV 2 F | 1.8 | uM |
| HSV 2 R | 1.8 | uM |
| HSV 2 P | 0.8 | uM |
| Trizma | 2 | mM |
| STACHYOSE | 2.5 | % M/V |
| PEG | 0.5 | % M/V |

Master Mix Recipe (2.5× cake formulation) dried to 5 µL volume final (1×).

| REAGENT | CAKE CONCENTRATION (2.5 x) | |
|---|---|---|
| MgCl2 | 10 | mMols/L |
| BSA | 625 | mg/L |
| dUTPS(dUTP/dNTP mixture) | 0.5 | mMols/L |
| Taq | 100000 | UNITS/L |
| Trizma | 25 | mMols/L |
| STACHYOSE | 2.5 | % (M/v) |
| PEG | 0.5 | % (M/v) |

Both compositions were freeze dried as described in Example 2, but in separate micro-amp style vessels.

The resulting compositions were used to amplify a DNA target (derived from HSV 1 and 2) using custom primers in combination with dual labelled fluorogenic probes for each target using the 5' nuclease assay process.

The primer probe pots were resuspended in 12.5 µL of water to which 12.5 µL of either template or water (for no amplification controls) was added and mixed. 12.5 µL was transferred to the core master mix pot and mixed before transfer to an ECO plate. The mixture was amplified on the Illumina ECO thermal cycler using the following parameters:

PCR Parameters

| | Denature | 98° C. 600 seconds |
|---|---|---|
| | Amplification | 95° C. 5 seconds |
| | | 62° C. 35 seconds, |
| | | Optical Read in FAM and HEX channels |
| 45 Cycles | | |

Figure 3:
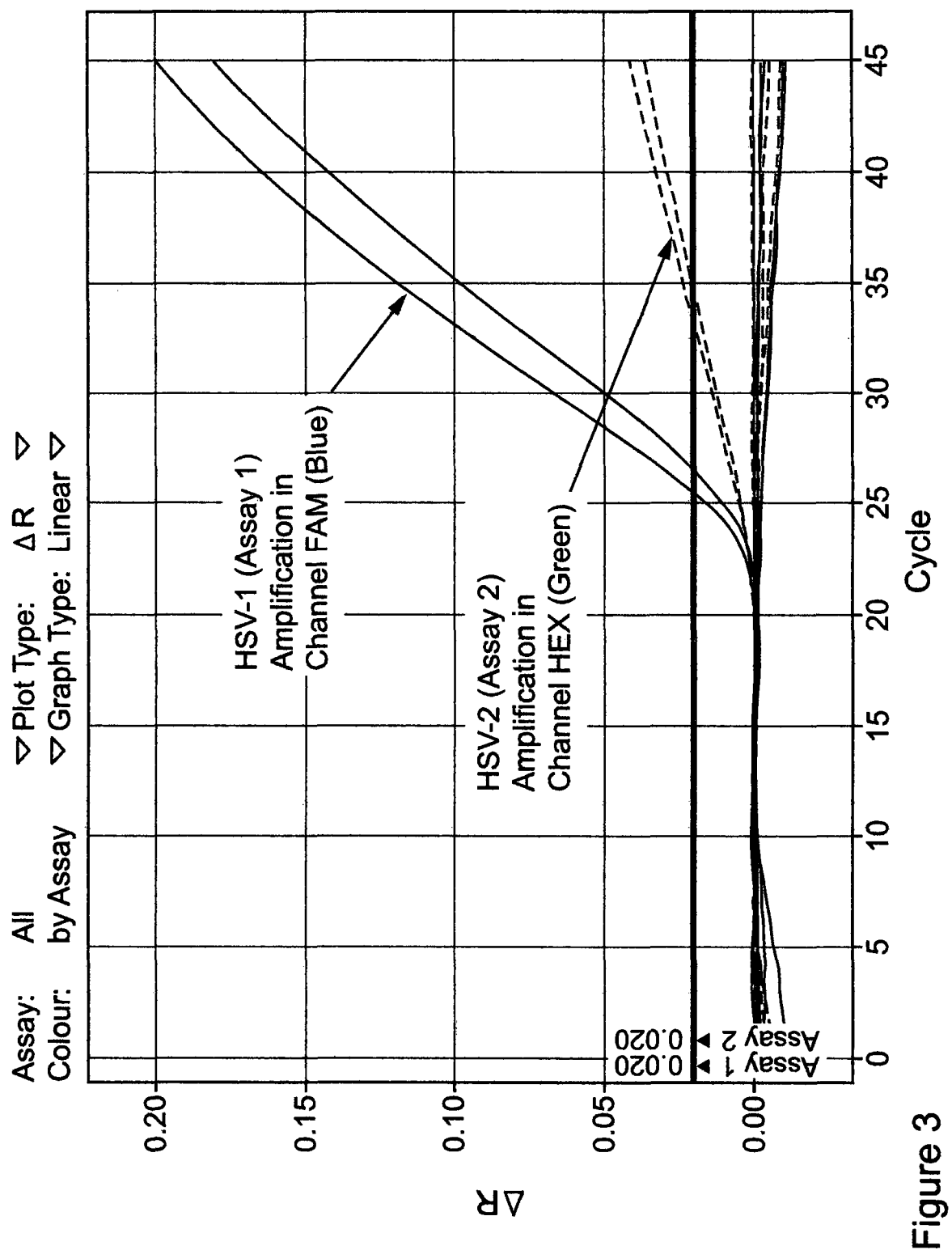
FIGS. 3-5 shows the results of amplification reactions carried out using various PCR enzymes which had been incorporated into compositions in accordance with the invention.

The results are shown in FIG. 3. They illustrate efficient amplification for both templates tested.

EXAMPLE 5

Generation and Testing of other Lyophilised PCR Reaction Mixtures

This example illustrates the generation and use of a lyophilised core master mix preparations according to the invention.

A first mastermix included as the enzyme a high fidelity recombinant polymerase Pfu DNA dependent DNA polymerase in a suitable buffer composition.

| Reagent | Cake Concentration (2X) | Final Concentration |
| --- | --- | --- |
| Trizma | 20 mM | 10 mM |
| BSA | 500 ng/µl | 250 ng/µl |
| dUTP/dNTP | 0.4 mM | 0.2 mM |
| Pfu enzyme | 0.04 U/µl | 0.02 U/µl |
| Stachyose | 2.5% | 1.25% |
| PEG | 0.5% | 0.25% |

The composition was freeze dried as described in Example 2 in a glass lyovial. The resulting mixture was resuspended in resuspension buffer that was able to provide dissolution and an active complete PCR reaction mixture. This mixture was then used to amplify a DNA target (derived from bacteriophage λ) using custom primers in combination with SYBR® Green-1 DNA binding dye to a final concentration of 1:10,000 of reference solution. The mixture was amplified on the Genie thermal cycler using:
PCR Parameters

| | Denature | 98° C. 30 seconds | |
| --- | --- | --- | --- |
| | Amplification | 98° C. 10 seconds | |
| | | 55° C. 30 seconds | |
| | | 72° C. 30 seconds | Optical Read X5 |
| 45 Cycles | | | |
| | Melt | 50° C. 20 seconds | |
| | | 95° C. 10 seconds | Continuous read −1 Rate = 0.1° C./second |

Figure 4:
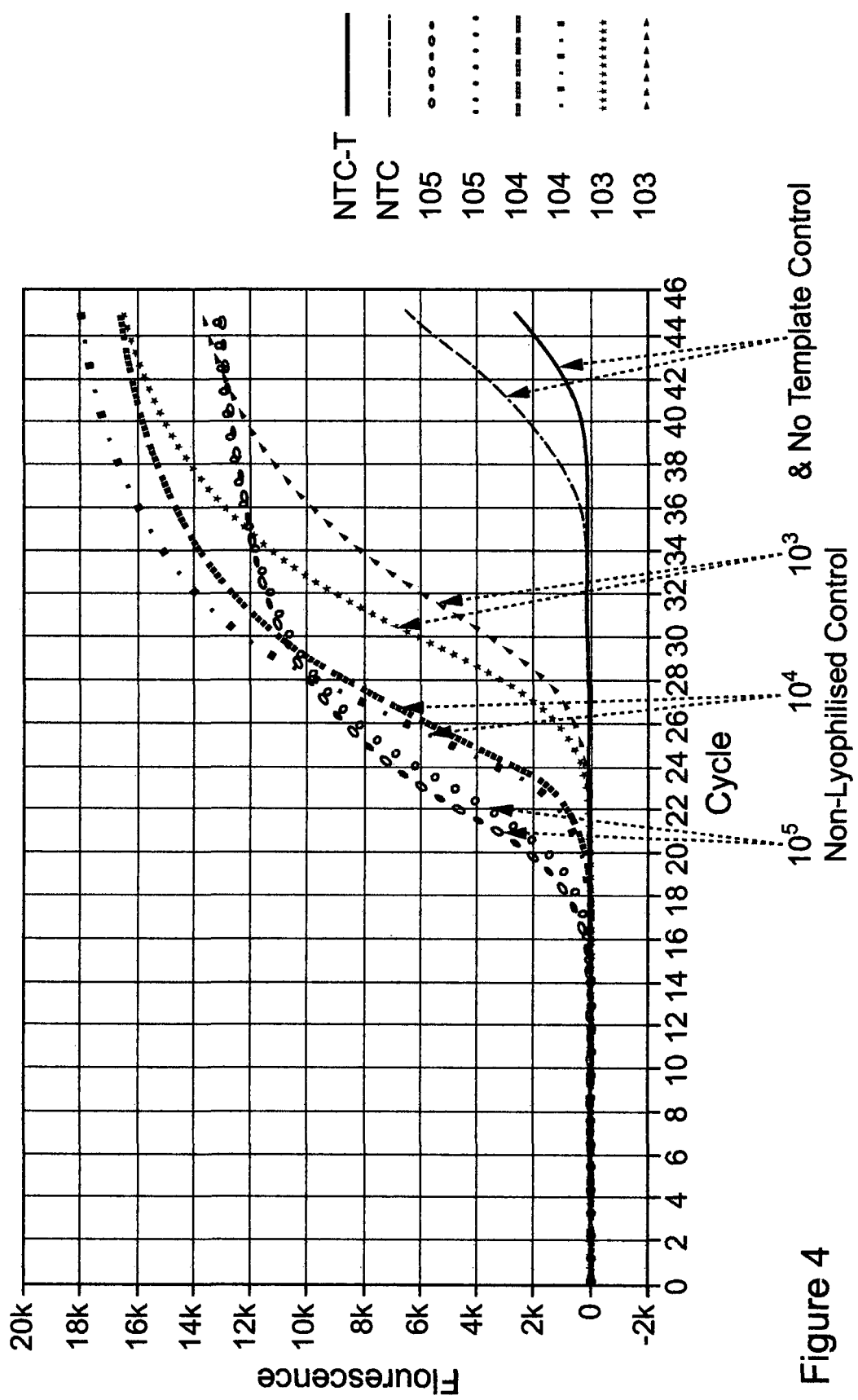

The data shows three 10-fold dilutions (labelled 10^5, 10^4, & 10^3) of template and a no-template control in duplicate amplifications. The results illustrated in FIG. 4 show efficient amplification across the tested target template concentrations.

In a second experiment, a chemically modified hot start polymerase Taq DNA dependent polymerase in combination with a thermo-stable MMuLV RNA dependant DNA RNase H-polymerase was used as the enzyme. This was combined with other reagents including salts and appropriate concentrations of stachyose to form a PCR mastermix. This was dried in a glass lyovial using a method as described in Example 2.

The resulting mixture was used to amplify a RNA target (derived from rat 18s RNA) using custom primers in combination with dual labelled fluorogenic probes for each target using the 5' nuclease assay process. The mixture was amplified on the Genie thermal cycler using:
PCR Parameters

| | RT-Step | 48° C. 600 seconds | |
| --- | --- | --- | --- |
| | Denature | 95° C. 900 seconds | |
| | Amplification | 95° C. 20 seconds | |
| | | 60° C. 60 seconds | Optical Read X10 |
| 45 Cycles | | | |

Figure 5:
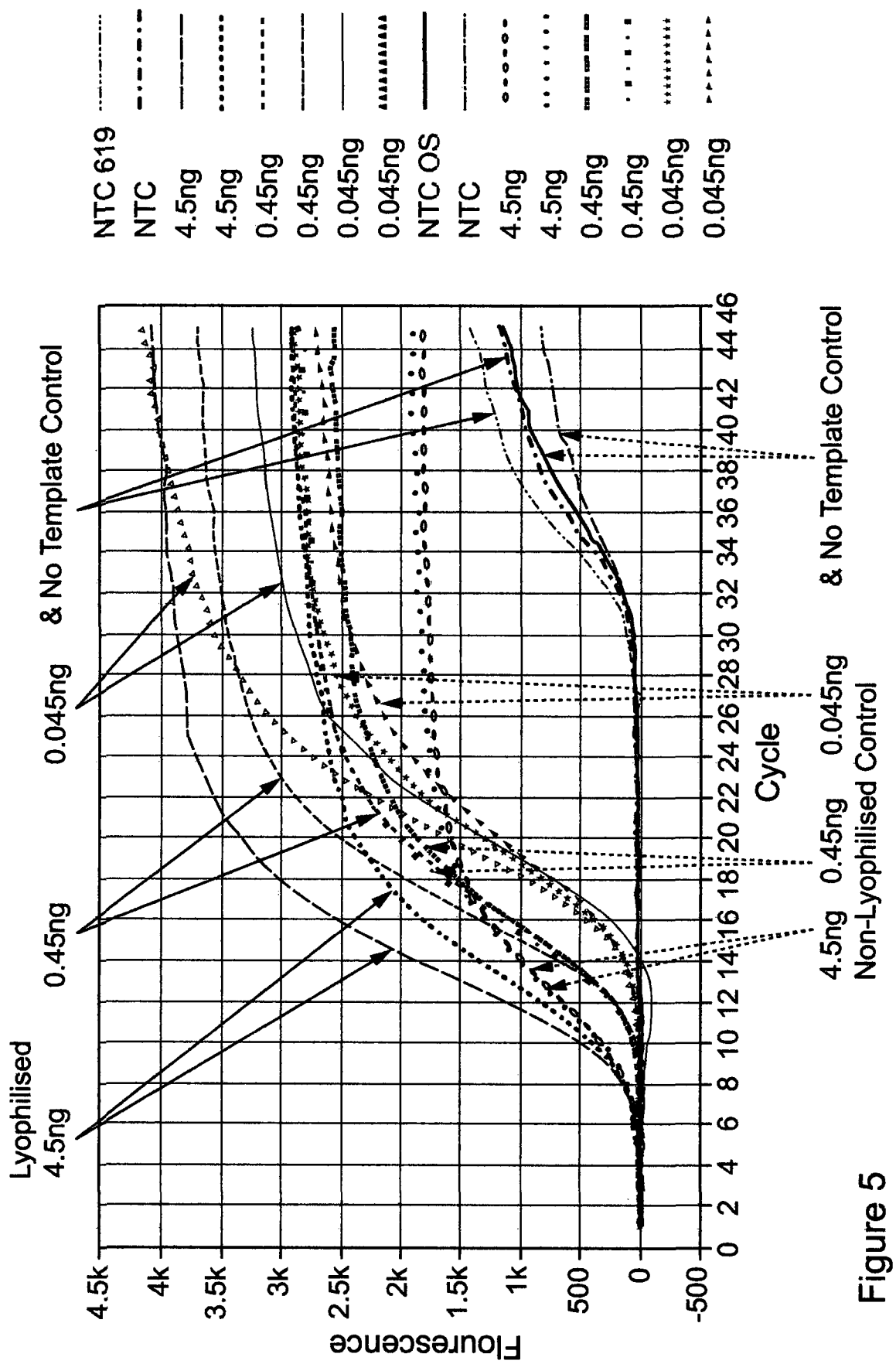

The amplifications were carried out at three 10-fold dilutions (labelled 4.5 ng (per reaction), 0.45 ng (per reaction), 0.045 ng (per reaction) of template and a no-template control in duplicate amplifications. The results are shown in FIG. 5 solid lines are reactions prepared using lyophilised master mix. The dotted line shows a commercial 2× master mix (non-lyophilised) control. The results are substantially equivalent.

EXAMPLE 6

Alternative Separate Compositions

As described above, one embodiment of the invention includes the use of a core lyophilised PCR master with a lyophilised resuspension buffer, which forms a second composition. This resuspension buffer may also be lyophilised using the same freeze drying procedure as the PCR master, but in a separate vial (although alternative drying techniques may be used as described above). This means that salts required for the buffer composition in the final reaction, but which could be inhibitory, for example, to the stability of the polymerases during and post drying to be kept away from the enzymes until required. Likewise some of the enzyme cofactor, which in this case is magnesium ions in the form of magnesium chloride may be dried in this buffer.

This is illustrated here by an example of the use of an anti-Taq antibody mediated hot start Taq DNA dependent polymerase lyophilised master mix for use in combination with the reconstitution buffer. The reconstitution buffer mixture and lyophilised PCR master is dried using the same process but in separate vessels.

Reconstitution buffer cake recipe Recipe (2× cake formulation), dried to 12.5 µL volume final.

| REAGENT | CAKE CONCENTRATION (2x) | |
| --- | --- | --- |
| Magnesium Chloride | 4 | mMols/L |
| Ammonium Sulphate | 20 | mMols/L |
| Potassium Chloride | 20 | mMols/L |
| STACHYOSE | 2.5 | % M/V |
| PEG | 0.5 | % M/V |

PCR Master Mix Recipe (2× cake formulation) dried to 12.5 µL volume final (2×). The final PCR reaction would be 25 µL.

| REAGENT | CAKE CONCENTRATION (2 x) | |
| --- | --- | --- |
| MgCl2 | 6 | mMols/L |
| BSA | 500 | mg/L |
| dUTPS (dUTP/dNTP mixture) | 0.4 | mMols/L |
| Taq | 80000 | UNITS/L |
| Trizma | 20 | mMols/L |
| STACHYOSE | 2.5 | % (M/v) |
| PEG | 0.5 | % (M/v) |

The two separate dried compositions as set out above, may be collected together in a kit.

A number of reconstitution regimes and solute permutations are possible. For example, in a first embodiment, the reconstitution buffer cake is re-suspended using only water to a 2× composition. The resulting mixture is used to effect dissolution of the lyophilised master mix to a 2× solution. The complete solution will form a 2× mixture that may be further diluted with primers, probes and template to carry out a PCR.

Alternatively, the reconstitution buffer cake is re-suspended using a primer-probe cocktail to a 2× composition. The resulting mixture is used to effect dissolution of the lyophilised master mix to a 2× solution. The complete solution will form a 2× mixture that may be further diluted with template to carry out a PCR.

The invention claimed is:

1. A dried composition having a cake three-dimensional structure which is resistant to collapse in an environment of 75% humidity, the composition comprising:
   (i) a polymerase that is useful in a nucleic acid amplification reaction; and
   (ii) stachyose;
   wherein the dried composition is free of gelatin and is in a freeze-dried form, and the polymerase is a thermostable polymerase.

2. The dried composition of claim 1 wherein the polymerase is a reverse-transcriptase or is chemically modified or blocked so that it is inactivated until subject to an initial heat activation step.

3. The dried composition of claim 1 which is for carrying out a polymerase chain reaction and which further comprises at least one of the following further reagents:
   (i) a buffer;
   (ii) a metal salt;
   (iii) nucleotides which may be fluorescently labelled;
   (iv) a blocking compound;
   (v) an anti-oxidant and/or anti-maillard reagent;
   (vi) a primer useful in a polymerase chain reaction which is optionally labelled with a fluorescent label;
   (vii) a probe useful in detection of a polymerase chain reaction which is optionally labelled with one or more fluorescent labels;
   (viii) a fluorescent dye;
   (ix) an anti-Taq antibody that binds to the active site of the polymerase and inactivates it at ambient temperature, but denatures and dissociates from the enzyme at elevated temperatures;
   (x) a pyrophosphate salt and a pyrophosphatase enzyme;
   (xi) a nucleic acid that is able to act as an internal control for an amplification reaction;
   (xii) a primer that is able to amplify the nucleic acid of item (xi); or
   (xiii) an isothermal polymerase.

4. The dried composition of claim 3 which is in the form of a freeze-dried cake which comprises two or more distinct layers, and wherein at least one of said further reagents is comprised within one distinct layer within the freeze-dried cake.

5. The dried composition of claim 1 which further comprises a polymeric compound that is able to stabilize a freeze-dried cake, wherein the polymeric compound is selected from the group consisting of polyethylene glycol, polyvinylpyrrolidine, and polysaccharides.

6. A kit comprising the dried composition of claim 1 and a second composition comprising a reagent for use in a reaction with said polymerase.

7. The kit of claim 6 wherein the second composition is in freeze-dried form.

8. The kit of claim 7 wherein said second composition comprises stachyose and a reagent mixture for use in a reaction with said polymerase.

9. A method for preparing the dried composition of claim 1, wherein the method comprises forming a solution by combining the polymerase and stachyose and optionally one or more further components, and freeze-drying the solution.

10. The method of claim 9 wherein the polymerase is in the form of a solution from which glycerol has been substantially removed.

11. The method of claim 10 wherein at least one of a detergent, an antioxidant or an anti-reducing agent is added to the polymerase after removal of glycerol and before combination with stachyose.

12. The method of claim 9 which comprises one or more further components and wherein the method comprises (i) freezing a first solution of stachyose and either one or more of said further components or the polymerase to form a first frozen layer, (ii) adding a second solution of stachyose and a different one of said further components or the polymerase and freezing the second solution into a second frozen layer, (iii) optionally repeating step (ii) until all components of the composition are present in distinct frozen layers, and (v) freeze-drying the resultant structure.

13. The method of claim 9 wherein the solution is divided amongst multiple reaction vessels so that each vessel contains sufficient reagents to carry out a single reaction using the polymerase, and freeze-dried within said vessels.

14. A method for carrying out a chemical or biochemical reaction using a polymerase, said method comprising forming a reaction mixture by addition of a liquid and any additional components necessary for carrying out said reaction to the dried composition of claim 1, and subjecting the thus formed solution to suitable reaction conditions.

15. The method of claim 14 wherein the chemical or biochemical reaction is a polymerase chain reaction.

16. A method for enhancing the stability of a composition comprising a polymerase, said method comprising freeze-drying a mixture comprising the polymerase with stachyose as a glass forming agent, wherein the mixture is free of gelatine.

* * * * *